United States Patent [19]
Patel et al.

[11] Patent Number: 5,106,736
[45] Date of Patent: Apr. 21, 1992

[54] ENZYMATIC PROCESS FOR ENANTIOMERSPECIFIC PREPARATION OF MERCAPTO ALKANOIC ACID COMPOUNDS

[75] Inventors: Ramesh N. Patel, Bridgewater; Laszlo J. Szarka, East Brunswick, both of N.J.

[73] Assignee: E.R. Squibb & Sons, Inc., Princeton, N.J.

[21] Appl. No.: 690,406

[22] Filed: Apr. 23, 1991

[51] Int. Cl.$^5$ .................... C12P 13/00; C12P 17/10; C12P 11/00; C12R 1/00
[52] U.S. Cl. ................. 435/106; 435/107; 435/117; 435/121; 435/130; 435/170; 435/171; 435/180; 435/196; 435/197; 435/822; 435/874; 435/877; 435/911; 435/917
[58] Field of Search ............ 435/121, 117, 280, 130, 435/106, 107

[56] References Cited

U.S. PATENT DOCUMENTS

| | | |
|---|---|---|
| 4,105,776 | 8/1978 | Ondetti et al. |
| 4,316,906 | 2/1982 | Ondetti et al. |
| 4,601,987 | 7/1986 | Klibanov et al. |
| 4,629,701 | 12/1986 | Sakimae et al. ............ 435/280 |
| 4,800,162 | 1/1989 | Matson. |
| 4,857,469 | 8/1989 | Ishimura et al. ............ 435/138 |
| 4,885,246 | 12/1989 | Mori et al. ............ 435/123 |
| 4,898,822 | 2/1990 | Asada et al. ............ 435/136 |

FOREIGN PATENT DOCUMENTS

| | | | |
|---|---|---|---|
| 3245695 | 10/1988 | Japan ............ | 435/130 |
| 05328 | 9/1987 | PCT Int'l Appl. . | |
| 8705328 | 9/1987 | World Int. Prop. O. ............ | 435/130 |

OTHER PUBLICATIONS

Wang, Y. F. et al., Tetrahedron Letters, vol. 25, No. 44, pp. 4999–5002 (1984) "Bifunctional chiral synthons via biochemical methods 4 chiral precursors to (+)-biotin and (−)-A-factor."

Tombo, G. M. R. et al., Tetrahedron Letters, vol. 27, No. 47, pp. 5707–5710 (1986) "Synthesis of both enantiomeric forms of 2-substituted 1,3-propanediol monoacetates starting from a common prochiral precursor, using enzymatic transformations in aqueous and in organic media."

*Primary Examiner*—Herbert J. Lilling
*Attorney, Agent, or Firm*—Suzanne E. Babajko

[57] ABSTRACT

An enzymatic process for the enantiomer-specific preparation of mercapto alkanoic acids by stereoselective hydrolysis of mercapto or thioester alkanoic acid esters.

32 Claims, No Drawings

ENZYMATIC PROCESS FOR ENANTIOMERSPECIFIC PREPARATION OF MERCAPTO ALKANOIC ACID COMPOUNDS

FIELD OF THE INVENTION

The instant invention relates to a novel enzymatic process for the enantiomer-specific preparation of mercapto alkanoic acid compounds from mercapto or thioester alkanoic acid esters. The instant invention thus relates to the resolution of mercapto or thioester alkanoic acid ester enantiomeric mixtures.

BACKGROUND OF THE INVENTION

Optically active carboxylic acids represented by the formula I:

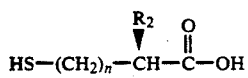

where $R_2$ is alkyl, cycloalkyl, aralkyl or aryl, and n is 1 or 2, are useful, for example, as intermediates for the synthesis of various physiologically active materials. For example, the compound D(−)-3-mercapto-2-methylpropanoic acid having the formula:

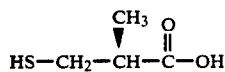

can serve as a key intermediate in the synthesis of 1-(2S)-3-mercapto-2-methylpropionyl]-L-proline (captopril), having the formula:

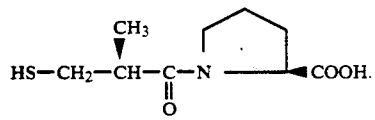

and [1(R*),2α,4α]-1-[3-(benzoylthio)-2-methyl-1-oxopropyl]-4-(phenylthio)-L-proline (zofenopril), having the formula:

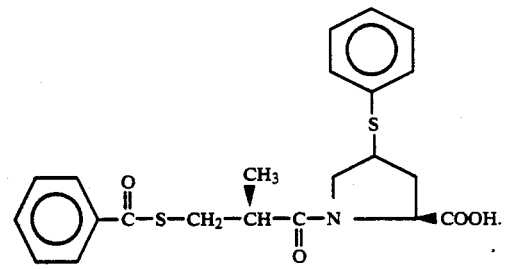

The beneficial activity of captopril and zofenopril depends on the configuration of the mercaptoalkanoyl moiety and the compounds of the S configuration are about 100 times more potent than the corresponding R-enantiomers. Thus, the S-enantiomers illustrated by formula I are much more desirable for such purposes than their R-enantiomer counterparts.

Prior art processes have utilized chemical and enzymatic resolution procedures. For example, carboxylic acids of the formula:

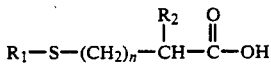

where $R_1$ is hydrogen or

and $R_3$ is alkyl, cycloalkyl, aralkyl or aryl, are prepared as racemic mixtures which can be separated into the R- and S-enantiomeric forms using chemical resolving agents. The so-provided S intermediates can then be used to prepare the desired products. Chemical resolution techniques have the distinct disadvantage, however, that large amounts of very expensive resolving agents are required. Additionally, the processes themselves are cumbersome and the yield is relatively low.

Alternatively, racemic compounds of the formula:

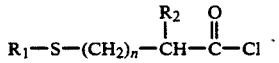

can be directly coupled to X (which is L-proline in the case of captopril, and L-4-phenylthioproline in the case of zofenopril) to produce diastereomers of the general formula:

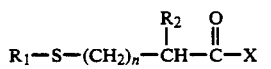

The SS-diastereomer of these compounds can be isolated. Thereafter, the sulfhydryl or benzoylthio groups corresponding to captopril and zofenopril, respectively, can be provided to the left side of the molecule by known methods. However, a drawback to this process is that an equal amount of the RS-diastereomer is formed which must be discarded. This is highly undesirable in view of the cost of L-proline and derivatives thereof.

U.S. Pat. No. 4,629,701 provides resolved carboxylic acids by subjecting a compound containing both a carboxylic acid ester as well as a thioester group to an enzyme capable of asymmetrically hydrolyzing such a compound. It was found that while the carboxylic acid ester moiety is hydrolyzed to the acid form, the racemic compound is also resolved into the S or R configuration in improved yields and at lower costs than possible with chemical resolution techniques. Hydrolysis of the thioester group, as well as the carboxylic acid ester group is not, however, disclosed by this patent.

SUMMARY OF THE INVENTION

In accordance with the instant invention, a novel process is provided for preparing a mixture (a) or a mixture (b), wherein mixture (a) comprises an S-enantiomeric acid having the formula Ia:

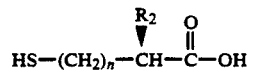

where $R_2$ is alkyl, cycloalkyl, aralkyl or aryl, and n is 1 or 2, admixed with an R-enantiomeric ester, and mixture (b) comprises an R-enantiomeric acid having the formula Ib:

$$HS-(CH_2)_n-CH(R_2)-C(=O)-OH \quad \text{Ib}$$

where $R_2$ and n are as defined above for formula Ia, admixed with an S-enantiomeric ester. The instant process comprises the step of treating a mixture of R and S enantiomers of a compound having the formula II:

$$R_1-S-(CH_2)_n-CH(R_2)-C(=O)-OR_4, \quad \text{II}$$

where $R_1$ is hydrogen or $$R_3-C(=O)-;$$

$R_3$ and $R_4$ are independently alkyl, cycloalkyl, aryl or aralkyl; and $R_2$ and n are as defined above for formula Ia, preferably a racemic mixture, with an enzyme or microorganism capable of catalyzing the stereoselective hydrolysis of compounds of the formula II to provide a reaction medium containing the mixture (a) or the mixture (b). The S-enantiomeric compounds of mixtures (a) or (b) may then be separated from the respective R-enantiomeric compounds, and recovered.

Thus, hydrolysis of both the ester bond $$(-C(=O)-OR_4),$$

as well as the thioester bond $$(-S-C(=O)-R_3)$$

when $R_1$ is $$-C(=O)-R_3,$$

of the R or S enantiomer of the compound of the formula II is provided by the instant process to provide a compound of the formula Ia or Ib.

It is preferred to prepare the mixture (a) by the process of the instant invention.

DESCRIPTION OF THE PREFERRED EMBODIMENTS

The following definitions apply throughout this application.

The term "alkyl", as used herein alone or as part of a larger group, refers to straight or branched chain carbon groups of 1 to 25 carbon atoms, preferably 1 to 6 carbon atoms, which may be substituted by appropriate substituents, that is, substituents providing compounds suitable for use in the present invention, or preferably, are unsubstituted.

The term "cycloalkyl", as used herein alone or as part of a larger group, refers to groups containing 5 to 7 carbon atoms, which may be substituted by appropriate substituents or, preferably, are unsubstituted.

The term "aryl", as used herein alone or as part of a larger group, refers to monocyclic or bicyclic aromatic groups containing from 6 to 10 carbon atoms in the ring portion such as phenyl, naphthyl, and substituted phenyl or naphthyl containing substituents such as nitro, halogen, methyl or alkoxy groups on the aromatic ring.

The term "formula II compound", as used herein, refers to a mixture, preferably racemic, of R- and S-enantiomers of the formula II.

The term "stereoselective hydrolysis", as used herein, refers to the preferential hydrolysis, relative to its enantiomer, of either the R-enantiomer of the compound of formula II or the S-enantiomer of the compound of formula II.

In accordance with the present invention, it has been found that, in the presence of one or more catalyzing hydrolytic enzymes or microorganisms producing same, the stereoselective hydrolysis of a stereoisomeric, preferably racemic, mixture of compounds of the formula II is achieved. The instant process may provide, as the hydrolytic product, an S-enantiomeric acid of the formula Ia, and an unreacted R-enantiomeric ester having the formula IIIa:

$$R_1-S-(CH_2)_n-CH(R_2)-C(=O)-OR_4 \quad \text{IIIa}$$

when the mixture (a) is formed or, as the hydrolytic product, an R-enantiomeric acid of the formula Ib, and an unreacted S-enantiomeric ester having the formula IIIb:

$$R_1-S-(CH_2)_n-CH(R_2)-C(=O)-OR_4 \quad \text{IIIb}$$

when the mixture (b) is formed.

The enzymatic resolution process of the present invention is advantageous in that it can provide high yields of S-enantiomeric compounds, preferably S-enantiomeric acids of the formula Ia, with high optical purity. When the reaction is catalyzed at ambient temperature, for example, an enantiomeric purity of greater than about 98% may be obtained. These features make the process of the present invention very attractive for use in preparing optically active S-enantiomeric compounds, particularly S-enantiomeric acids of the formula Ia, such as D(−)-3-mercapto-2-methylpropanoic acid useful in the preparation of captopril and zofenopril.

Methods for obtaining the racemic starting material of the formula II are known. For example, a compound of the formula IV:

$$R_1-SH \quad \text{IV}$$

may be coupled to a compound of the formula V:

$$H_2C=C(R_2)-C(=O)-OR_4 \quad \text{V}$$

or a compound of the formula VI:

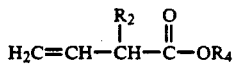

VI in the presence or absence of a suitable solvent, such as hexane, heptane or isopropanol, under the usual conditions for conducting such an addition reaction. Starting mixtures which are other than racemic may, for example, be prepared by addition of R- or S-enantiomer(s) of the compound of formula II in other than equal portions to a racemic mixture prepared as above. Use of a racemic mixture of the starting material of formula II is, however, preferred.

The present process is preferably carried out in an aqueous system such as water or an aqueous buffer.

The enzyme or microorganism employed in the present process may be any enzyme or microorganism having the ability to catalyze the stereoselective hydrolysis of esters of the formula II as described herein. Various enzymes, such as esterases and lipases, regardless of origin or purity, are suitable for use in the present invention. The enzyme may, for example, be in the form of animal or plant enzymes or mixtures thereof, cells of microorganisms, crushed cells, extracts of cells, or of synthetic origin.

With respect to the use of microorganisms, the process of the present invention may be carried out using any microbial cellular material having the ability to catalyze the stereoselective hydrolysis of the compounds of formula II as described herein. The cells may be used in the form of intact wet cells or dried cells such lyophilized, spray-dried or heat-dried cells. Cells may also be used in the form of treated cell material such as ruptured cells or cell extract. The cells or cellular materials may be employed in the free state or immobilized on a support such as by physical adsorption or entrapment.

Exemplary genera of microorganisms suitable as sources of catalyzing enzymes include Mucor, Escherichia, Staphylococcus, Agrobacterium, Rhizopus, Aspergillus, Nocardia, Streptomyces, Trichoderma, Candida, Rhodotorula, Torulopsis, Bacillus, Alcaligenes, Pseudomonas, Brevibacterium, Geotrichum, Enterobacter, Chromobacteriuum, Arthrobacter, Microbacterium, Mycobacterium, Saccharomyces, Penicillium, Botrytis, Chaetomium, Ophiobolus, Cladosporium and the like. The use of microorganisms of the genera Pseudomonas, Candida, Geotrichum, and Chromobacterium is preferred. In particular, microorganisms of the genera Pseudomonas and Chromobacterium are preferred for the preparation of mixture (a).

Specific microorganisms suitable for use in the present process include *Chromobacterium viscosum, Pseudomonas aeuriginosa* such as ATCC 25619, *Pseudomonas fluorescens, Pseudomonas putida* such as ATCC 31303, *Pseudomonas ovalis, Escherichia coli, Staphylococcus aureus, Alcalienes faecalis, Streptomyces griseus, Psedomonas cepacia, Candida rugosa* such as ATCC 14830, *Geotrichum candidum* such as ATCC 32345, *Streptomyces clavuligerus, Nocardia erthropolis, Nocardia asteraides, Mycobacterium phlei, Agrobacterium radiobacter, Aspergillus niger, Rhizopus oryzae* and the like. The use of species of the Pseudomonas genus, especially sp. ATCC 21808, and the Chromobacteriuum genus, especially Chromobacterium viscosum ATCC 6918, is particularly preferred for the preparation of mixture (a). Two or more, as well as a single, species of microorganism may be employed when carrying out the instant process.

The term "ATCC" as used herein refers to the accession number of the American Type Culture Collection, 12301 Parklawn Drive, Rockville, Md., 20852, the depository for the organism referred to.

When microorganisms are employed for catalysis, the instant process may, for example, be carried out as a single-step process comprising simultaneous fermentation and transformation of the compound of formula II, or as a two-step fermentation and transformation process. In a single-step process, the microorganisms used may be grown in an appropriate medium containing carbon and nitrogen sources. The starting formula II compound may be added to the microbial cultures, and transformation of the formula II compound to mixture (a) or mixture (b) continued until a desired conversion is obtained.

In a two-step process, microorganisms may, in the first step, be grown in an appropriate medium by fermentation exhibiting the desired hydrolytic enzyme activity. The cells may then be suspended, for example, in an appropriate buffered solution to prepare cell suspensions. The formula II compound may be mixed with the microbial cell suspensions, and transformation of formula II compound to the desired product, that is, mixture (a) or mixture (b), catalyzed by the suspensions. The reaction may be continued until a desired conversion of the formula II compound is obtained.

Culture media may be employed which provide nutrients necessary for the growth of the microbial cells. A typical medium for growth includes necessary carbon sources, nitrogen sources, and trace elements.

Carbon sources include sugars such as maltose, lactose, glucose, fructose, glycerol, sorbitol, sucrose, starch, mannitol, and the like; organic acids such as sodium acetate, sodium citrate, and the like; amino acids such as sodium glutamate, and the like; alcohols such as ethanol, propanol, and the like.

A carbon source may be added during transformation. Also, formula II compound may be added as an inducer during growth of the microorganisms.

Nitrogen sources include N-Z Amine A, corn steep liquor, soy bean meal, beef extracts, molasses, baker's yeast, tryptone, nutrisoy, sodium nitrate, ammonium sulfate, and the like.

Trace elements include phosphates and magnesium, manganese, calcium, cobalt, nickel, iron, sodium, and potassium salts.

Typical preferred media are as follows:

| Medium 1 | |
|---|---|
| Beef extract | 5 g |
| Peptone | 7.5 g |
| NaCl | 2.5 g |
| Glucose | 5 g |
| Yeast extract | 1.5 g |
| Malt extract | 1.5 g |
| Ucon antifoam* | 0.1 g |
| Water | 1 Liter |
| Medium 2 | |
| Cerelose hydrate | 7.92 Kg |
| Ammonium sulfate | 1.35 Kg |
| Yeast extract | 180 g |
| Ucon antifoam* | 72 g |
| Corn steep liquid | 7.2 Liter |
| Water | 180 Liter |

*polysiloxanes

Microorganisms may be grown in Medium 1, for example, for 24 to 48 hours at 280 RPM agitation and 28° to 30° C., for inoculum development. A fermentor containing Medium 2 may then be inoculated with microorganisms grown in Medium 1. An exemplary arrangement for fermentation of approximately 190 L of Medium 2 may, for example, be that where a 250 L fermentor is employed which is equipped with three Rushton (flat-blade turbine) impellers, a sparger, a pH controller, a dissolved oxygen (DO) meter, a temperature controller, a foam sensor with automatic antifoam addition, and inlet and exhaust air filters.

The efficiency of the process may be affected by both the initial amount of formula II substrate used and by the timing and amount of substrate added during the process. Substrate may be added batchwise, for example, every 1 to 12 hours, or continuously during the transformation process by growing cells in a one-step fermentation, or by cell-suspensions of microorganisms as in a two-step fermentation/transformation process.

Preferred initial concentrations of formula II substrate are those between about 10 mg/ml and about 1000 mg/ml, particularly between about 10 mg/ml and 50 mg/ml, based on cell concentration. Additional substrate is preferably added in amounts such as those between about 5 mg/ml and 50 mg/ml, especially between about 5 mg/ml and about 10 mg/ml.

The pH of the medium may be maintained between about 4.0 and about 9.0, preferably between about 6.5 and about 7.5, during growth of microorganisms and during the transformation process.

Buffers such as tris-HCl, phosphates, sodium acetate and the like may be used to prepare suspensions of microbial cells to conduct the transformation process.

The temperature of the reaction mixture is a measure of the heat energy available for the transformation process. The reaction temperature may be selected and maintained to ensure that there is sufficient energy available for the process. A temperature range from about 15° C. to 60° C., especially from about 25° C. to 50° C., is preferred for the transformation.

The agitation and aeration of the reaction mixture affects the amount of oxygen available during the transformation process which may be conducted, for example, in shake-flask cultures or fermenter tanks during growth of microorganisms in a single-step or two-step process. An agitation range of from about 50 to about 1000 RPM is preferable, with a range of from about 50 to about 500 RPM being most preferred. Aeration rates of from about 1 to about 5 volumes of air per volume of media per minute (i.e., 1 to 5 v/vt) are preferred.

The optimum reaction time for the transformation process generally ranges from about 12 to about 168 hours, preferably 24 to 48 hours, measured from the time of initially treating the substrate formula II compound with a microorganism to the time at which a desired conversion of formula II compound to mixture (a) or mixture (b) is achieved.

With respect to the use of one or more hydrolytic enzymes, whether or not derived from microorganisms, the process of the instant invention may be carried out using any enzyme having the ability to catalyze the stereoselective hydrolysis of the compounds of formula II as described herein. Conditions such as temperature, pH, etc. discussed above with respect to the use of microorganisms may be employed. The hydrolytic enzyme may be derived by isolation from a microorganism, synthetically or from any other appropriate source.

Exemplary, commercially available enzymes suitable for use in the present invention include lipases, such as Amano $P_{30}$ (*Pseudomonas fluorescens*), Amano AY-30 (*Candida cylindracea*), Amano N (*Rhizopus niveus*), Amano R (*Penicillium sp.*), Amano FAP (*Rhizopus oryzae*), Amano AP-12 (*Aspergillus niger*), Amano MAP (*Mucor meihei*), Amano GC-4 (*Geotrichum candidum*), Sigma L-0382 (*porcine pancreas*), Sigma L-3001 (Wheat germ), Sigma L-1754 (*Candida cylindracea*), Sigma L-0763 (*Chromobacterium viscosum*) and Amano K-30 (*Aspergillus niger*). Exemplary enzymes derived from animal tissue include esterase from pig liver, α-chymotrypsin and pancreatin from pancreas. When (+)-3-acetylthio-2-methylpropionic methyl ester is employed as the substrate formula II compound of the instant process, it is preferred that an enzyme other than an *Aspergillus niger* (e.g. Amano AP) lipase be employed. For the preparation of mixture (a), enzymes derived from microorganisms of the genera Pseudomonas or Chromobacterium are preferred. It is particularly preferred to employ enzyme derived from *Pseudomonas sp.* ATCC 21808 or *Chromobacterium viscosum* ATCC 6918.

The hydrolytic enzyme may be employed in the free state or immobilized on a support. The enzyme may, for example, be adsorbed onto a suitable carrier, e.g., oxirane-acrylic beads (Eupergit C), diatomaceous earth (porous Celite Hyflo Supercel), microporous polypropylene (Enka Accurel® polypropylene powder), or a nonionic polymeric adsorbent such as Amberlite® XAD-2 (polystyrene) or XAD-7 (polyacrylate) from Rohm and Haas Co. Immobilizing the enzyme has the effects of controlling the enzyme particle size, and preventing aggregation of the enzyme particles. Additionally, and preferably, immobilized enzyme may be readily reused in the instant process. Adsorption onto a support such as Celite Hyflo Supercel may be accomplished, for example, by precipitating an aqueous solution of the enzyme with cold acetone in the presence of the support followed by vacuum drying, or in case of a nonionic polymeric adsorbent, incubating enzyme solutions with adsorbent on a shaker for a desired time, removing excess solution and drying the enzyme-adsorbent resins under vacuum. It is particularly preferred to employ enzyme immobilized on an oxirane-acrylic bead support such as Eupergit C in the process of the instant invention.

The enzyme employed, when derived from a microorganism, may be derived either by extracellular expression of the enzyme by the microorganism or by separating intracellularly-prepared enzyme from cellular materials. The microbial genera and species discussed above with respect to the use of microorganisms are exemplary of microbial enzyme sources.

While it is desirable to use the least amount of enzyme possible, the amount of enzyme required will vary depending upon the specific activity of the enzyme employed. The enzyme is, in general, preferably added to the reaction solution in an amount of from about 0.01 to about 10 mg of enzyme per mg of formula II compound, most preferably, from about 0.1 to about 2 mg enzyme per mg of formula II compound.

The reaction time may be appropriately varied depending upon the amount of enzyme used and its specific activity. Reaction times may be reduced by increasing the reaction temperature and/or increasing the amount of enzyme added to the reaction solution.

S-enantiomeric acids of the formula Ia or S-enantiomeric esters may be isolated from the reaction mixtures (a) and (b), respectively, and purified by known methodologies such as extraction, distillation, crystallization, column chromatography, and the like. The term "resolved", as used in reference to these compounds, contemplates compounds which are at least partially, preferably completely, resolved from the enantiomeric mixture.

The resolved S-enantiomeric acids or esters prepared by the instant process may be used in the preparation of pharmacologically active compounds, especially in the preparation of antihypertensives. The resolved S-enantiomeric acids may be employed directly or protected or modified prior to subsequent use, such as by acylation of the mercapto group with a group such as an alkanoyl, cycloalkanoyl, aralkanoyl or aroyl group. To allow acylation through the carboxylic group in a subsequent use, hydrolysis may be employed as appropriate to form a free carboxylic acid group on the resolved S-enantiomeric esters of mixture (b), for example, by conventional hydrolytic methods. Preparation of the mixture (a) is thus preferred as such a subsequent hydrolysis step may be avoided.

Exemplary antihypertensives preparable employing the resolved S-enantiomeric acids or esters of the instant process include those described in U.S. Pat. Nos. 4,105,776 and 4,316,906. These patents, reciting antihypertensives and methods of preparation thereof, are incorporated herein by reference.

The resolved acid of formula Ia where $R_2$ is methyl and n is 1, or protected forms thereof, may, for example, be used to acylate L-proline having the formula VII:

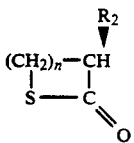
VII forming captopril. Alternatively, the resolved acid of formula Ia may be dehydrated to form a thiolactone of the formula VIII:

VIII

The thiolactone VIII may thereafter be used to acylate L-proline of formula VII to obtain the desired product.

Similarly, to provide zofenopril, the compound of formula Ia where $R_2$ is methyl and n is 1 or protected forms thereof may be used to acylate a compound of the formula IX:

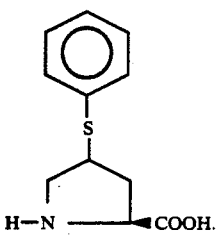
IX

Alternatively, the compound of formula Ia where $R_2$ is methyl and n is 1 in which the mercapto group has been acylated with a benzoyl group may be coupled with a compound of the formula X:

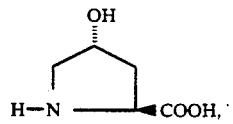
X or protected forms thereof, to provide a compound of the formula XII:

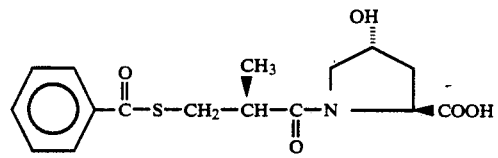
XII which can thereafter be treated with a compound of the formula XIII:

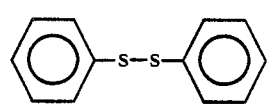
XIII or a compound of the formula XIV:

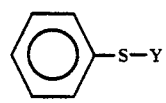
XIV where Y is an activating group such as succinimide or pthalamido or a halide such as Cl or Br to provide zofenopril.

The acylation of compounds VII, IX or X with, for example, the resolved acid of formula Ia may be effected in the presence of a coupling agent such as dicyclohexylcarbodiimide or the like, or the acid may be activated by formation of its mixed anhydride, symmetrical anhydride, acid chloride, acid ester or use of Woodward reagent K, N-ethoxycarbonyl-2-ethoxy-1,2-dihydroquinoline or the like. For a review of the methods for acylation, see *Methoden der Organischen Chemie* (Houben-Weyl), Vol. XV, part II, page 1 et seq. (1974).

The process will now be further described by the following examples. These examples are illustrative only, and are in no way intended to limit the scope of the instant claims.

EXAMPLE 1

Preparation of D(—)-3-Mercapto-2-methyl propanoic acid

The substrate for this process was DL-(—)-3-acetylthioisobutyric acid methyl ester. The structural formula of this substrate is:

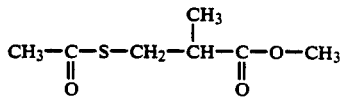

The structural formula of the desired title product, D(—)-3-mercapto-2-methyl propanoic acid, is:

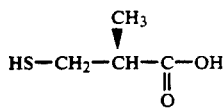

Bacterial cultures of *Pseudomonas aeuriginosa* ATCC 25619, *Pseudomonas sp.* ATCC 21808, *Pseudomonas putida* ATCC 31303, *Candida rugosa* ATCC 14830 *Geotrichum candidum* ATCC 32345 and *Chromobacterium viscosum* ATCC 6918 were used to conduct the transformation of the substrate to the title product.

The microorganisms were maintained in vials in liquid nitrogen. For routine development of inoculum, one vial was inoculated into 100 ml of Medium 1 (described above) in 500-ml flasks, and incubated at 28° C. to 30° C. and 250 to 300 RPM (revolutions per minute) on a shaker for 24 to 48 hours. After growth of the microorganisms, 10 ml of the cultures were inoculated into 500-ml flasks containing 100 ml of Medium 1 and incubated at 28° C. to 30° C. and 250 to 300 RPM on a shaker.

Various microorganisms (Table 1) were grown in Medium 2 (described above) for 48 to 72 hours at 28° C. to 30° C. and 250 to 300 RPM on a shaker. The cells were harvested and suspended in 0.05M phosphate buffer, pH 6.8. 10% w/v Wet cell-suspensions were prepared. The cell-suspensions (25 ml) were supplemented with 20 mg/ml of substrate and the transformations were conducted at 30° C., 250 RPM for 24 hours. The pH was maintained at 6.8 to 7.0 during the transformations. Periodically, 0.5 ml samples were taken and diluted with methanol (4.5 ml) and vortexed for 2 minutes.

3 ml of each of the mixtures were centrifuged in a microfuge, and the supernatant collected, passed through a 0.2 μm LID/X filter, and analyzed to determine the reaction yield by HPLC.

HPLC Conditions

Column: HP hypersil C18, 20×4.6 cm, 5 micron
Mobile phase: 30% methanol, 70% water containing 0.05% (85%) $H_3PO_4$
Temperature: 40° C.
Flow Rate: 1 ml/min
Detection: 230 nm
Injection vol: 5 μl The optical purity of the title product was determined by GC assay as follows:

5 ml of each of the mixtures were centrifuged at 6000 RPM (Sorvall SS34) to remove cells. The supernatant was collected, the pH adjusted to 2.0 with 10% $H_2SO_4$, and the medium then extracted with 2 volumes of ethyl acetate. The collected ethyl acetate layer was evaporated under nitrogen to obtain an oily residue which was used to prepare diastereomers using thionyl chloride and d-2-octanol. The optical purity of the title product was determined by the method described in *J. Chromatography*, v. 394, p. 388 (1987), which entails acetylation of the sulfhydryl group with acetic anhydride, esterification of the carboxyl group with d-2-octanol and gas chromatography to separate the diastereomers.

GC Conditions

Column: HP fused silica capillary column, cross-linked methyl silicone, 15 m long, 1.0 μm film thickness, 0.31 mm I.D. (HP #19091Z-215)
Injection Temperature: 250° C.
Detector: FID, 250° C.
Column Temperature: 160° C., isothermal
Split Flow: 50 ml/min.
Injection Volume: 2 μl
Carrier Gas: Helium, 25 ml/min.

The results of these analyses are presented in Table 1. The results of Table 1 demonstrate that all of the tested organisms converted the substrate to the desired title product. *Pseudomonas sp.* ATCC 21808 was found to provide the best conversion of substrate to title product in terms of both yield and optical purity (see Table 1).

TABLE 1

Resolution of DL(±)-3-acetylthioisobutyric acid methyl ester to D(−)-3-mercapto-2-methylpropanoic acid

| Microorganisms | Reaction Time (Hours) | Reaction Yield (M %) | Optical Purity (%) |
|---|---|---|---|
| *Pseudomonas aeuriginosa* ATCC 25619 | 24 | 32 | 90 |
| *Pseudomonas sp.* ATCC 21808 | 24 | 46 | 98 |
| *Pseudomonas putida* ATCC 31303 | 24 | 30 | 97 |
| *Candida rugosa* ATCC 14830 | 48 | 25 | 80 |
| *Geotrichum candidum* ATCC 32345 | 48 | 22 | 89 |
| *Chromobacterium viscosum* ATCC 6918 | 24 | 30 | 96 |

EXAMPLE 2

Preparation and Immobilization of Cell Extracts and use of Immobilized Enzyme: Preparation of D(−)-3-Mercapto-2-methyl propanoic acid Cells (25 grams, wet frozen) of *Pseudomonas sp.* ATCC 21808 and *Pseudomonas putida* ATCC 31303 were suspended in 100 ml of 1M potassium phosphate buffer, pH 7.0.

The cell suspensions were disintegrated by passing through a French Press at 15,000 psi pressure. The disintegrated cell suspensions were centrifuged in a Sorvall (SS-34 rotor) at 6000 RPM for 15 minutes. Sedimented cells and cell debris were discarded. The supernatant solutions were centrifuged in a Sorvall (SS-34 rotor) at 15,000 RPM for 40 min. The supernatant solutions obtained after centrifugation are referred to as the cell extracts. To 20 ml of the cell extracts in 1M potassium phosphate buffer, pH 7.0, 0.1% sodium azide and 5 g of Eupergit C were added. The flask containing this mixture was incubated at room temperature for 48 hours.

Immobilized enzyme was washed on glass frit, first with 50 ml of deionized water (in two portions), then with 150 ml of 1M NaCl (in 3–4 portions), and finally twice with the 50 mM potassium phosphate buffer, pH 7.0, containing 0.1% azide. 13.5 g of immobilized enzyme stored at 5° C. were used to conduct the transformation of the substrate DL (±)-3-acetylthioisobutyric acid methyl ester to the title product, as described in Example 1. The results obtained are shown in Table 2. Immobilized enzyme was reused in the second cycle.

The results shown in Table 2 demonstrate the conversion of substrate to title product for the tested immobilized enzymes.

TABLE 2

Resolution of DL($\pm$)-3-acetylthioisobutyric acid methyl ester to D(−)-3-mercapto-2-methylpropanoic acid by Immobilized Enzyme:

| Enzyme Source | Cycle # | Reaction Time (Hours) | Reaction Yield (M %) | Optical Purity (%) |
|---|---|---|---|---|
| Immobilized Pseudomonas sp. ATCC 21808 Extracts | 1 | 24 | 46 | 98 |
|  | 2 | 24 | 45 | 98 |
| Immobilized Pseudomonas putida ATCC 31303 Extracts | 1 | 24 | 33 | 97 |
|  | 2 | 24 | 32 | 97 |

What is claimed is:

1. A process for preparing a mixture (a) or a mixture (b), wherein
said mixture (a) comprises an S-enantiomeric acid having the formula Ia:

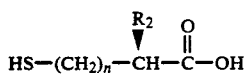

where $R_2$ is alkyl, cycloalkyl, aralkyl or aryl, and n is 1 or 2, admixed with an R-enantiomeric ester, and said mixture (b) comprises an R-enantiomeric acid having the formula Ib:

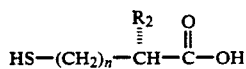

where $R_2$ and n are as defined for said formula Ia, admixed with an S-enantiomeric ester,
comprising the step of treating a mixture of R and S enantiomers of a compound having the formula II:

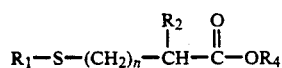

where $R_1$

$R_3$ and $R_4$ are independently alkyl, cycloalkyl, aryl or aralkyl; and
$R_2$ and n are as defined for said formula Ia; with an enzyme or microorganism capable of catalyzing the stereoselective hydrolysis of compounds of the formula II to provide said mixture (a) or said mixture (b), with the proviso that, when said formula II compound is ($\pm$)-3-acetylthio-2-methylpropionic methyl ester, an enzyme other than *Aspergillus niger* lipase is employed.

2. The process of claim 1, wherein a racemic mixture of R and S enantiomers is employed as the starting material of said formula II.

3. The process of claim 1, wherein said mixture (a) is prepared.

4. The process of claim 1, comprising the further step, subsequent to said treatment, of separating and recovering the S-enantiomeric acid of formula Ia of said mixture (a), or the S-enantiomeric ester of said mixture (b).

5. The process of claim 1, wherein said enzyme is selected from esterases and lipases.

6. The process of claim 1, wherein said microorganism is selected from the genera Mucor, Escherichia, Staphylococcus, Agrobacterium, Rhizopus, Aspergillus, Nocardia, Streptomyces, Trichoderma, Candida, Rhodotorula, Torulopsis, Bacillus, Alcaligenes, Pseudomonas, Brevibacterium, Geotrichum, Enterobacter, Chromobacterium, Arthrobacter, Microbacterium, Mycobacterium, Saccharomyces, Penicillium, Botrytis, Chaetomium, Ophiobolus and Cladosporium.

7. The process of claim 3, wherein said microorganism is selected from the genera Pseudomonas or Chromobacterium.

8. The process of claim 6, wherein said microorganism is selected from *Pseudomonas aeuriginosa*, *Pseudomonas sp.* ATCC 21808, *Chromobacterium viscosum*, *Pseudomonas fluorescens*, *Pseudomonas putida*, *Pseudomonas ovalis*, *Escherichia coli*, *Staphylococcus aureus*, *Alcaligenes faecalis*, *Streptomyces griseus*, *Pseudomonas cepacia*, *Candida rugosa*, *Geotricium candidum*, *Streptomyces clavuligerus*, *Nocardia erthropolis*, *Nocardia asteraides*, *Mycobacterium phlei*, *Agrobacterium radiobacter*, and *Rhizopus oryzae*.

9. The process of claim 1, wherein said enzyme is selected from Amano P (*Pseudomonas fluorescens*), Amano AY-30 (*Candida cylindracea*), Amano N (*Rhizopus niveus*), Amano R (*Penicillium sp.*), Amano FAP (*Rhizopus oryzae*), Amano MAP (*Mucor meihei*), Amano GC-4 (*Geotrichum candidum*), Sigma L-0382 (*porcine pancreas*), Sigma L-3001 (Wheat germ), Sigma L-1754 (*Candida cylindracea*), and Sigma L-0763 (*Chromobacterium viscosum*).

10. The process of claim 3, wherein said enzyme is derived from a microorganism of the genera Pseudomonas or Chromobacterium.

11. The process of claim 10, wherein said enzyme is immobilized on a support.

12. The process of claim 1, wherein said process is conducted in an aqueous medium.

13. The process of claim 3, wherein said S-enantiomeric acid of formula Ia is

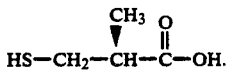

14. The process of claim 4, wherein said S-enantiomeric acid of the mixture (a) or said S-enantiomeric ester of the mixture (b) is subsequently employed in the preparation of an antihypertensive.

15. The process of claim 13, comprising the further step, subsequent to said treatment, of coupling said compound of formula Ia with a compound of the formula:

to prepare a compound having the formula:

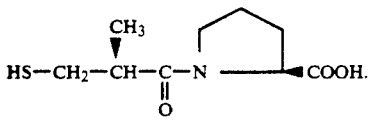

16. The process of claim 13, comprising the further step, subsequent to said treatment, of dehydrating said compound of formula Ia to form a thiolactone of the formula

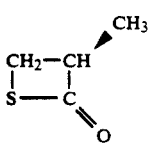

and thereafter acylating a compound of the formula

with said thiolactone to provide a compound having the formula

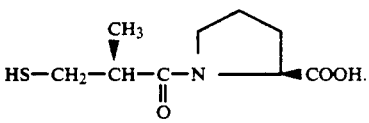

17. The process of claim 1, wherein said mixture (a) comprises an unreacted R-enantiomeric ester of the following formula IIIa:

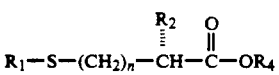

where n, $R_1$, $R_2$ and $R_4$ are as defined in formula II, and said mixture (b) comprises an unreacted S-enantiomeric ester of the following formula IIIb:

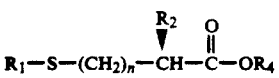

where n, $R_1$, $R_2$ and $R_4$ are as defined in formula II.

18. A process for preparing a mixture (a) or a mixture (b), wherein
said mixture (a) comprises an S-enantiomeric acid having the formula Ia:

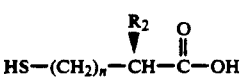

where $R_2$ is alkyl, cycloalkyl, aralkyl or aryl, and n is 1 of 2, admixed with an R-enantiomeric ester, and said mixture (b) comprises an R-enantiomeric acid having the formula Ib:

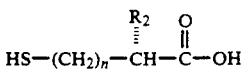

where $R_2$ and n are as defined for said formula Ia, admixed with an S-enantiomeric ester,
comprising the step of treating a mixture of R and S enantiomers of a compound having the formula II:

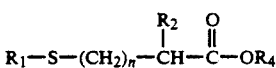

where $R_1$ is hydrogen;
$R_4$ is alkyl, cycloalkyl, aryl or aralkyl; and
$R_2$ and n are as defined for said formula Ia;
with an enzyme or microorganism capable of catalyzing the stereoselective hydrolysis of compounds of the formula II to provide said mixture (a) or said mixture (b), with the proviso that, when $R_2$ and $R_4$ are both the same or different alkyl groups and a microorganism or enzyme derived therefrom is employed, (i) said microorganism or enzyme source is selected from the genera Pseudomonas or Candida and said mixture (a) is prepared, or (ii) said microorganism or enzyme source is selected from the genera Chromobacterium or Geotrichum.

19. The process of claim 18, wherein a racemic mixture of R and S enantiomers is employed as the starting material of said formula II.

20. The process of claim 18, wherein said mixture (a) is prepared.

21. The process of claim 18, comprising the further step, subsequent to said treatment, of separating and recovering the S-enantiomeric acid of formula Ia of said mixture (a), or the S-enantiomeric ester of said mixture (b).

22. The process of claim 18, wherein said enzyme is selected from esterases and lipases.

23. The process of claim 18, wherein $R_2$ and $R_4$ are both the same or different alkyl groups and a microorganism of enzyme derived therefrom is employed, where said microorganism or enzyme source is selected from the genus Chromobacterium.

24. The process of claim 23, wherein said microorganism or enzyme source is *Chromobacterium viscosum*.

25. The process of claim 18, wherein $R_2$ and $R_4$ are both the same or different alkyl groups and a microorganism or enzyme derived therefrom is employed, where said microorganism or enzyme source is selected from *Pseudomonas aeruginosa*, *Pseudomonas sp.* ATCC 21808, *Pseudomonas putida*, *Pseudomonas ovalis*, and *Pseudomonas cepacia*.

26. The process of claim 18, wherein $R_2$ and $R_4$ are not both alkyl.

27. The process of claim 18, wherein said enzyme is immobilized on a support.

28. The process of claim 18, wherein said process is conducted in an aqueous medium.

29. The process of claim 20, wherein said S-enantiomeric acid of formula Ia is

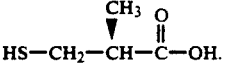

30. The process of claim 21, wherein said S-enantiomeric acid of the mixture (a) or said S-enantiomeric ester of the mixture (b) is subsequently employed in the preparation of an antihypertensive.

31. The process of claim 29, comprising the further step, subsequent to said treatment, of coupling said compound of formula Ia with a compound of the formula:

to prepare a compound having the formula:

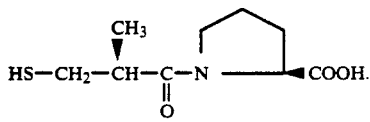

32. The process of claim 29, comprising the further step, subsequent to said treatment, of dehydrating said compound of formula Ia to form a thiolactone of the formula

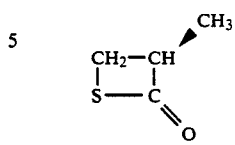

and thereafter acylating a compound of the formula

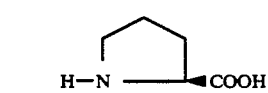

with said thiolactone to provide a compound having the formula

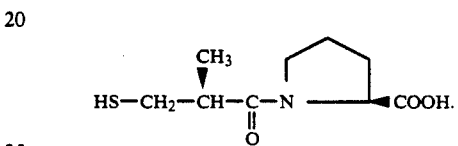

* * * * *